US00PP18967P2

(12) United States Plant Patent
Koppe

(10) Patent No.: US PP18,967 P2
(45) Date of Patent: Jun. 24, 2008

(54) ***BEGONIA* PLANT NAMED 'ELEKTRA PINK'**

(50) Latin Name: *Begonia×hiemalis*
Varietal Denomination: Elektra Pink

(75) Inventor: Lubbertus H. Koppe, Ermelo (NL)

(73) Assignee: Koppe Royalty B.V., Ermelo (NL)

( * ) Notice: Subject to any disclaimer, the term of this patent is extended or adjusted under 35 U.S.C. 154(b) by 2 days.

(21) Appl. No.: 11/489,219

(22) Filed: Jul. 19, 2006

(51) Int. Cl.
*A01H 5/00* (2006.01)

(52) U.S. Cl. ..... Plt./343

(58) Field of Classification Search ..... Plt./343
See application file for complete search history.

(56) References Cited

PUBLICATIONS

UpovROM PBR 20032160 Plant Variety Database for cultivar Elektra Pink 1 page.*

* cited by examiner

*Primary Examiner*—Annette H Para
(74) *Attorney, Agent, or Firm*—C. A. Whealy

(57) ABSTRACT

A new and distinct cultivar of *Begonia* plant named 'Elektra Pink', characterized by its upright and mounded plant habit; freely branching habit; double flowers that are dark pink in color and held above the foliage; and excellent postproduction longevity.

1 Drawing Sheet

Botanical designation: *Begonia×hiemalis.*
Cultivar denomination: 'Elektra Pink'.

BACKGROUND OF THE INVENTION

The present invention relates to a new and distinct cultivar of *Begonia* plant, botanically known as *Begonia×hiemalis,* commercially known as Elatior *Begonia,* and hereinafter referred to by the name 'Elektra Pink'.

The new *Begonia* is a product of a planned breeding program conducted by the Inventor in Ermelo, The Netherlands. The objective of the breeding program is to create new vigorous *Begonia* cultivars with excellent postproduction longevity.

The new *Begonia* originated from a cross-pollination made by the Inventor in Ermelo, The Netherlands in January, 1999 of an unnamed selection of *Begonia tuberhybrida,* not patented, as the female, or seed, parent with an unnamed selection of *Begonia socotrana,* not patented. The cultivar Elektra Pink was discovered and selected by the Inventor as a flowering plant from within the progeny of the stated cross-pollination in a controlled environment in Ermelo, The Netherlands in June, 1999.

Asexual reproduction of the new *Begonia* by cuttings harvested in a controlled environment in Ermelo, The Netherlands since June, 2000, has shown that the unique features of this new *Begonia* are stable and reproduced true to type in successive generations.

SUMMARY OF THE INVENTION

The cultivar Elektra Pink has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Elektra Pink'. These characteristics in combination distinguish 'Elektra Pink' as a new and distinct *Begonia:*

1. Upright and mounded plant habit.
2. Freely branching habit.
3. Double flowers that are dark pink in color and held above the foliage.
4. Excellent postproduction longevity.

Plants of the new *Begonia* differ primarily from plants of the female parent selection primarily in flower color as plants of the female parent selection have yellow-colored flowers.

Plants of the new *Begonia* differ from plants of the male parent selection in the following characteristics:

1. Plants of the new *Begonia* are more freely branching than plants of the male parent selection.
2. Plants of the new *Begonia* have darker green-colored leaves than plants of the male parent selection.
3. Plants of the new *Begonia* have darker pink-colored leaves than plants of the male parent selection.

Plants of the new *Begonia* can also be compared to plants of the cultivar Dark Netja, not patented. In side-by-side comparisons conducted in Ermelo, The Netherlands, plants of the new *Begonia* differed from plants of the cultivar Dark Netja in the following characteristics:

1. Plants of the new *Begonia* had narrower leaves than plants of the cultivar Dark Netja.
2. Flowers of plants of the new *Begonia* were more double than flowers of plants of the cultivar Dark Netja.
3. Plants of the new *Begonia* and the cultivar Dark Netja differed in flower color as plants of the cultivar Dark Netja had pink and white-colored flowers.

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia*.

The photograph at the top of the sheet comprises a side perspective view of a typical flowering plant of 'Elektra Pink' grown in a container.

The photograph at the bottom of the sheet is a close up view of typical leaves and flowers of 'Elektra Pink'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Ermelo, The Netherlands, under commercial practice in a glass-covered greenhouse during the spring and summer. Average day and night temperature was about 20° C. during the first three to four weeks then lowered to an average day and night temperature of 19° C. until flowering. Four weeks after planting rooted cuttings in 12-cm containers, one week of long nyctoperiods of 16 hours was given followed by short nyctoperiods of eight hours until flowering. Plants used for the photographs and the description were about 15 weeks from planting.

Botanical classification: *Begonia×hiemalis* cultivar Elektra Pink.

Commercial classification: Elatior *Begonia*.

Parentage:

*Female, or seed, parent.*—Unnamed selection of *Begonia tuberhybrida,* not patented.

*Male, or pollen, parent.*—Unnamed selection of *Begonia socotrana,* not patented.

Propagation:

*Type.*—By terminal vegetative cuttings.

*Time to develop roots.*—About 20 days at temperatures 20° C.

*Time to produce a rooted young plant.*—About 42 days at temperatures of 20° C.

*Root description.*—Fine, fibrous, well-branched; white/orange in color. Plants of the new *Begonia* have not been observed to form tubers.

Plant description:

*Plant form.*—Compact, upright and mounded plant habit, inverted triangle; freely branching with good stem and stem base strength. Flowers are double and abundant. Plants flower continuously.

*Growth habit.*—Moderate growth rate, vigorous. Suitable for 11 to 15-cm containers. Under optimal environmental and cultural conditions, usually about four months are required to produce proportional 13-cm potted plants from cuttings. Vegetative shoots are formed at basal nodes and flowering shoots are formed at upper nodes.

*Plant height.*—About 20 cm to 25 cm.

*Plant width.*—About 35 cm.

*Leaves.*—Arrangement: Simple, alternate. Developing leaves, length: About 3 cm to 4 cm. Developing leaves, width: About 8 cm to 9 cm. Fully expanded leaves, length: About 9 cm to 10 cm. Fully expanded leaves, width: About 15 cm to 17 cm. Shape: Roughly reniform; oblique. Apex: Acute. Base: Cordate; oblique. Margin: Double serrate. Texture, upper surface: Smooth, glabrous; margins, slightly pubescent. Texture, lower surface: Smooth, glabrous. Venation pattern: Palmate. Color: Developing leaves, upper surface: 147A. Developing leaves, lower surface: 191A slightly overlain with 178A. Fully expanded leaves, upper surface: Darker than 147A; venation, 144A to 144B. Fully expanded leaves, lower surface: 191A overlain with 178A; venation, 144A to 144B. Petiole length: About 1 cm to 9 cm. Petiole texture, upper and lower surfaces: Pubescent. Petiole color, upper and lower surfaces: Close to 146D.

Flower description:

*Flowering habit.*—Double flowers with numerous tepals arranged in axillary cymes. Usually six to eight flowers per cyme. Many cymes in flower simultaneously. Flowers positioned above the foliage. Flowering continuous.

*Natural flowering season.*—Plants will flower year round regardless of nyctoperiod, however plants flower earlier and more abundantly from mid-February until November in the Northern Hemisphere.

*Flowers.*—Shape: Rounded; rose-like. Diameter: About 4 cm to 5 cm. Depth (height): About 1.5 cm to 2 cm.

*Flower buds.*—Length: About 1.2 cm to 2 cm. Diameter: About 1.4 cm to 2.3 cm. Color: Close to 45D.

*Tepals.*—Arrangement: Rosette. Quantity per flower: Usually about 25 per flower. Size: Outer tepals, length: About 2.5 cm to 3 cm. Outer tepals, width: About 2.7 cm to 3.2 cm. Inner tepals, length: About 1.5 cm to 2 cm. Inner tepals, width: About 1.3 cm to 2 cm. Shape: Rounded flabellate. Apex: Rounded. Margin, outer and inner tepals: Slightly crenate. Texture, upper and lower surfaces: Smooth, glabrous; satiny. Color: When opening, upper and lower surfaces: Slightly darker than 61D. Fully opened, upper surface: Slightly lighter than 61D. Fully opened, lower surface: Close to 52D.

*Flower bracts.*—Quantity/arrangement: Two, opposite. Shape: Broadly cordate. Apex: Acute. Margin: Slightly serrate. Texture, upper and lower surfaces: Glabrous, smooth. Color, upper and lower surfaces: 146B overlain with close to 183A.

*Peduncles.*—Angle: Erect. Length: About 4 cm to 6 cm. Texture: Slightly pubescent. Color: Close to 144A.

*Pedicels.*—Angle: Erect. Length: About 5 mm to 3.5 cm. Texture: Pubescent. Color: More red than 161B.

*Reproductive organs.*—Stamens: None observed. Pistils: None observed.

*Seed/fruit.*—Seed and fruit production have not been observed as reproductive organs are not formed.

Postproduction longevity:

*Individual flowers.*—Generally about two to three weeks.

*Whole plants.*—About six weeks under interior conditions.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'Elektra Pink' as illustrated and described.

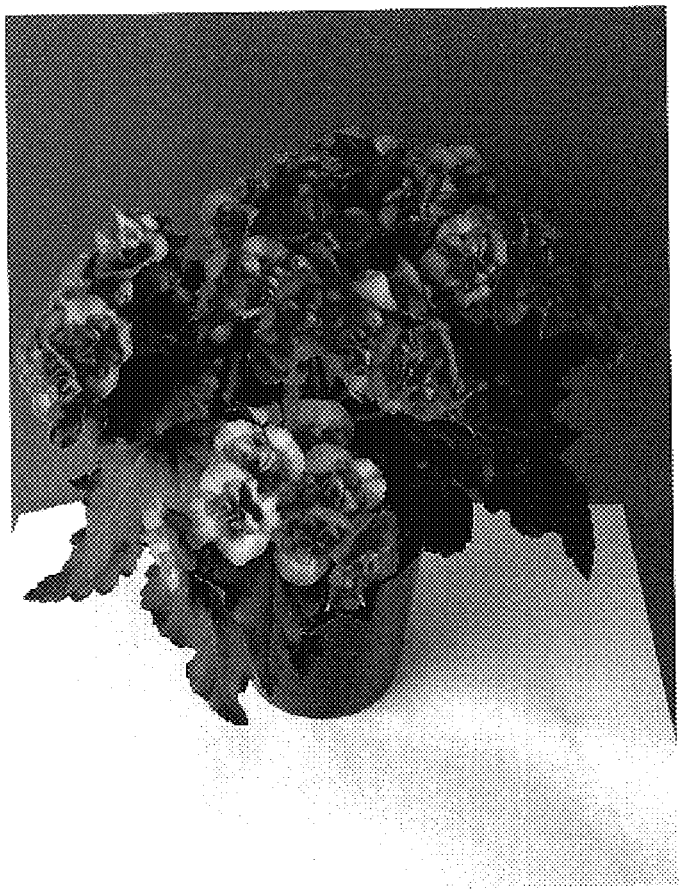
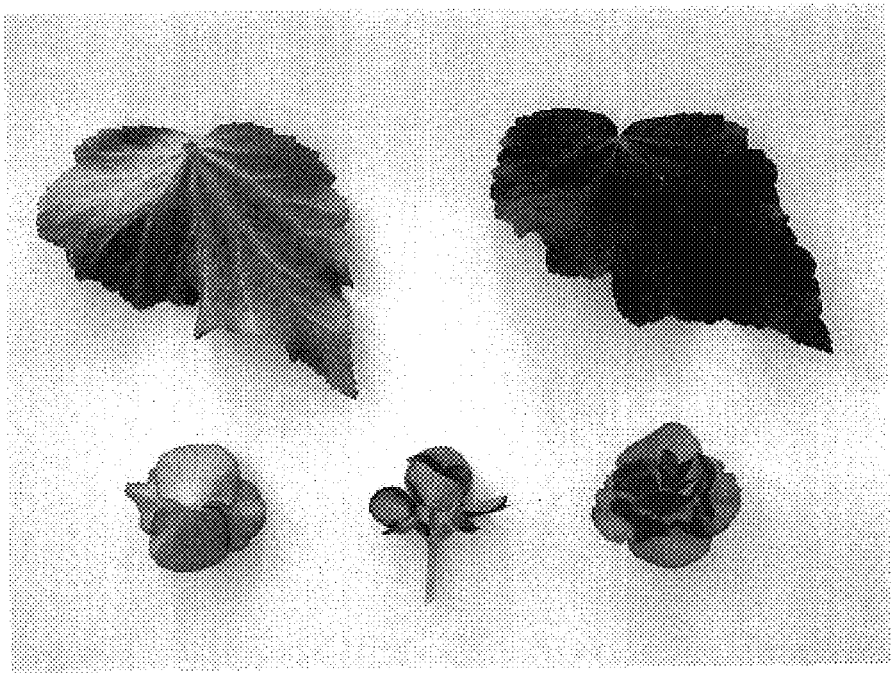

* * * * *